(12) United States Patent
Bodenschatz et al.

(10) Patent No.: US 6,713,659 B2
(45) Date of Patent: Mar. 30, 2004

(54) SELF-ADHESIVE BANDAGE

(75) Inventors: Stefan Bodenschatz, Buxtehude (DE); Arthur-Hugh Andrews, Kölln-Reisiek (DE); Anthony David Harman, Royston (GB)

(73) Assignee: Beiersdorf AG, Hamburg (DE)

( * ) Notice: Subject to any disclaimer, the term of this patent is extended or adjusted under 35 U.S.C. 154(b) by 243 days.

(21) Appl. No.: 09/732,371

(22) Filed: Dec. 7, 2000

(65) Prior Publication Data

US 2001/0001110 A1 May 10, 2001

Related U.S. Application Data

(63) Continuation of application No. PCT/EP99/03890, filed on Dec. 7, 2000.

(30) Foreign Application Priority Data

Jun. 9, 1998 (DE) .......................................... 198 25 577

(51) Int. Cl.⁷ ................................................. A61F 13/00
(52) U.S. Cl. ............................ 602/56; 602/41; 602/42; 602/43; 602/52
(58) Field of Search ............................ 602/41–47, 52, 602/54, 55, 56

(56) References Cited

U.S. PATENT DOCUMENTS

| 2,096,564 A | 10/1937 | Scholl |
| 5,228,458 A | 7/1993 | Ciacca |

FOREIGN PATENT DOCUMENTS

| DE | 25 17 790 A1 | 11/1976 |
| DE | 42 08 683 A1 | 10/1991 |
| EP | 0 453 413 A1 | 10/1991 |

OTHER PUBLICATIONS

Derwent Accession Number: 1976–85144X (English abstract of DE 25 17 790 A1 cited above).

Derwent Accession Number 1993–304194 (English abstract of DE 42 08 683 A1 cited above).

*Primary Examiner*—Nicholas D. Lucchesi
*Assistant Examiner*—Lalita M. Hamilton
(74) *Attorney, Agent, or Firm*—Norris McLaughlin & Marcus

(57) ABSTRACT

Self-adhesive bandage consisting of a flexible carrier with a self-adhesive coating applied on one side, characterized in that the carrier is provided with a large number of apertures, thus giving rise to individual segments linked by way of connecting bridges.

21 Claims, 4 Drawing Sheets

SELF-ADHESIVE BANDAGE

This application is a continuation of PCT/EP99/03890, filed Dec. 7, 2000.

The invention relates to a self-adhesively coated bandage for stabilizing and fixing joints and extremities.

For fractures of joints or extremities it is conventional to use a plaster cast in order to ensure the stabilization and/or fixing of the affected body part. The plaster cast restricts mobility to such an extent that the bone tissue is able to grow together again.

Plaster casts may also be used for ruptured ligaments in joints. In this case too, the dressing is intended to prevent any stress and/or movement.

Plaster casts of this kind may consist of plaster-of-Paris bandages or synthetic plaster bandages based on reactive resin. With both systems, curing is carried out by wetting with water. By means of curing, strength is achieved in conjunction with the reinforcing materials that are incorporated into the bandages.

These methods are known. However, they also have disadvantages for the patient and for the person applying the cast. Natural plaster bandages are relatively inexpensive but are heavy and of only limited durability. Synthetic plaster bandages have to be applied using gloves. Curing of the dressings takes up to 30 minutes. The synthetic plaster bandages must be packaged with great care since they cure on contact with atmospheric moisture.

Injuries to ligaments in joints can also be treated using the functional dressing technique, known as taping. The dressing technique is also a treatment method for the prophylaxis of injuries, diseases and disorders of the locomotor system. The aim of taping is to mimic the capsular ligament structures and so achieve selective support and stabilization. However, immobilization of the kind which is the aim of using plaster casts is not achieved by this means.

The actual tape dressing is applied in a strip formation comprising preferably non-elastic self-adhesive bands, known as straps, or in conjunction with self-adhesive bands having short-pull elasticity. It protects, supports and relieves threatened, damaged or disrupted parts of a functional unit. It permits functional loading within the pain-free sphere of movement but prevents extreme or painful movements.

Carrier materials which have proved useful are, in particular, nonwovens, wovens or knits coated with a pressure-sensitive adhesive. Even when two or more plies are applied, these bandages remain substantially flexible.

A bandage suitable for resting a body part is described in EP 0 352 095 B. The bandage consists of a substrate whose surfaces are impregnated with a curable liquid compound. The surfaces also have coverings which are permeable to water. The coverings preferably comprise a woven or nonwoven carrier comprising, inter alia, a fluorine compound or a silicone.

The object of the invention is to provide a bandage which on the basis of its configuration, material and properties is suitable for stabilizing and fixing joints and extremities.

This object is achieved by a bandage as defined in the main claim. The subclaims relate to advantageous developments of the bandage.

Accordingly, the self-adhesive bandage of the invention consists of a flexible carrier with a self-adhesive coating applied on one side, the carrier being provided with a large number of apertures, thus giving rise to individual segments linked by way of connecting bridges.

A film made of olefins or a foam made of polyurethane is preferably used as the carrier.

In one preferred embodiment the segments are convex in form. This ensures that, when a dressing is produced from the bandage, there is improved contact between the segments in the individual plies of the dressing.

In another preferred embodiment, the segments have a regularly shaped contour, and, in particular, are in the form of hexagons. In one preferred embodiment the hexagons have a width of 7 mm and are applied on the carrier at a spacing of 0.5 mm.

To save on weight, furthermore, the segments may also have recesses, which are preferably circular. In addition, the segments may consist of foamed material and/or may be blended with hollow beads or fibres.

The segments have a thickness, for example, of from 0.5 to 2 mm, in particular 1.5 mm.

Starting materials chosen for the segments are preferably plastics such as PET, PP, PE and other polymers, and also PVC if desired. Alternatively, PU (foamed/unfoamed) is possible, as are chitin and/or chitosan. Also suitable, finally, are multi-ply laminates: for example, a laminate comprising card/fibreboard/paper to which amino resins have been added.

Chitin (from the Greek χηιτον (chiton)=armour) comprises a polysaccharide which contains amino sugars and is isolated, in particular, from animal organisms, having the general formula $(C_8H_{13}NO_5)_x$, MW approximately 400,000. Chitin consists of chains of β-1,4-glycosidically linked N-acetyl-D-glucosamine (NAG) residues.

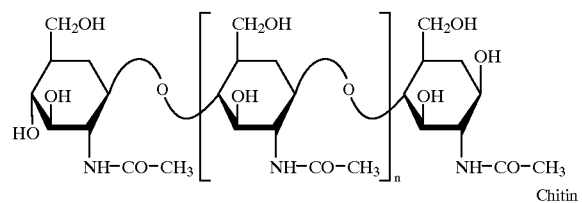

Chitin

In water, organic solvents and dilute alkalis and acids, chitin is insoluble. Strong acids cleave chitin into D-glucosamine (chitosamine) and acetic acid; cleavage by alkalis produces acetates and the weakly basic, deacetylated and partially depolymerized, crystallizable chitosan, which is soluble in dilute acids (except for sulphuric acid), aqueous methanol and glycerol and is also gel-forming and film-forming (in this respect see also Römpp Lexikon Chemie, 10th edition, under "Chitin", Stuttgart/New York: Georg Thieme Verlag, 1997).

The segments can be manufactured by being punched or cut from extruded films. Alternatively, they can be prepared by printing in the appropriate thickness.

The segments can also have the form of a pyramid or of a truncated cone, and also of further three-dimensional structures joined to one another by way of appropriate connecting bridges thus giving rise to a coherent carrier.

It has been found advantageous for the carrier then to have a thickness of from 0.3 to 1 mm, in particular 0.5 mm.

Manufacturing can be carried out by shaping the segments and the connecting bridges from a single extruded layer: for example, by cutting by means of rotating blades or by means of a water jet. Hot pressing is a further possibility.

On the side which is placed against the skin, the bandage is coated with one of the known, readily adhering self-adhesive compositions based on rubber or on synthetic polymers. The compositions advantageously have further properties, such as good skin compatibility or permeability to air and water vapour.

It has also been found particularly advantageous for the self-adhesive coating on the carrier to be a hotmelt adhesive composition having an activation temperature of less than 70° C., in particular from 50 to 60° C.

The self-adhesive coating has thicknesses, in particular, of about 50 μm.

In addition, an adhesion promoter can also be applied beneath the adhesive coating.

In another preferred embodiment the width of the bandage lies between 4 and 15 cm. The thickness of the bandage should preferably be within a range from 1 to 3 mm.

Before the bandage is used, the adhesive layer can be covered with a sheet material that has been given an anti-adhesive finish, such as, for example, siliconized paper or plastic film.

In a further preferred embodiment the self-adhesive bandage consists of a flexible carrier with a self-adhesive coating applied on both sides, the carrier being provided with a large number of apertures thus giving rise to individual segments linked by way of connecting bridges and the carrier being covered on one side with an auxiliary carrier.

In the case of this embodiment, the connecting bridges may also be entirely absent.

The auxiliary carrier consists preferably of a woven or knit based, in particular, on cotton, which is non-elastic in the lengthwise direction but may, if desired, have a slight transverse elasticity.

Overall, the result is a bandage which is non-elastic in the lengthwise direction but may be flexible in the transverse direction.

In one advantageous application of the bandage of the invention for stabilizing and fixing joints and extremities, rails, compressible cushions and/or wovens or nonwovens are placed on the skin below the bandage which is wound around the joints and/or extremities.

The advantages of the bandage over those known to date are that the bandage can be used to form a solid dressing having properties comparable to those of the known plaster casts.

Winding of the bandage in a plurality of plies produces a very strong dressing which greatly restricts the mobility of the joint or extremity affected.

On winding, the segments come to lie over one another in the manner of fish scales and are bonded to one another. Owing to the narrow connecting bridges, the bandage is readily shapable since the segments of one ply are able to shift relative to one another. It is certainly possible and in some cases desirable for bridges to break in the course of winding, thereby achieving further flexibility. The fish-scale-like structure, following winding and bonding of the individual plies, achieves a high stability although the resulting dressing is very much lighter than conventional natural plaster.

Especially when the bandage and/or the segments is or are coated with a hotmelt self-adhesive composition, it is possible to increase the effect considerably, since brief heating of the dressing, and thus of the segments, results in bonding of the segments to the underlying ply of the bandage, thus giving rise to an absolutely inflexible multi-ply dressing.

The aim is to achieve the required hardness of the dressing in approximately 15 minutes, this hardness being between 50 and 90% of the final hardness.

This strength also extends over a period of several weeks, as is required for the healing of common injuries.

Finally, through the choice of appropriate starting materials, the bandage also poses no barrier to X-rays.

Finally, the bandage can also be used again after it has been removed from the affected body part.

An advantageous embodiment of the bandage is illustrated in more detail with reference to the figures described below without thereby wishing unnecessarily to restrict the invention.

Figure 1:
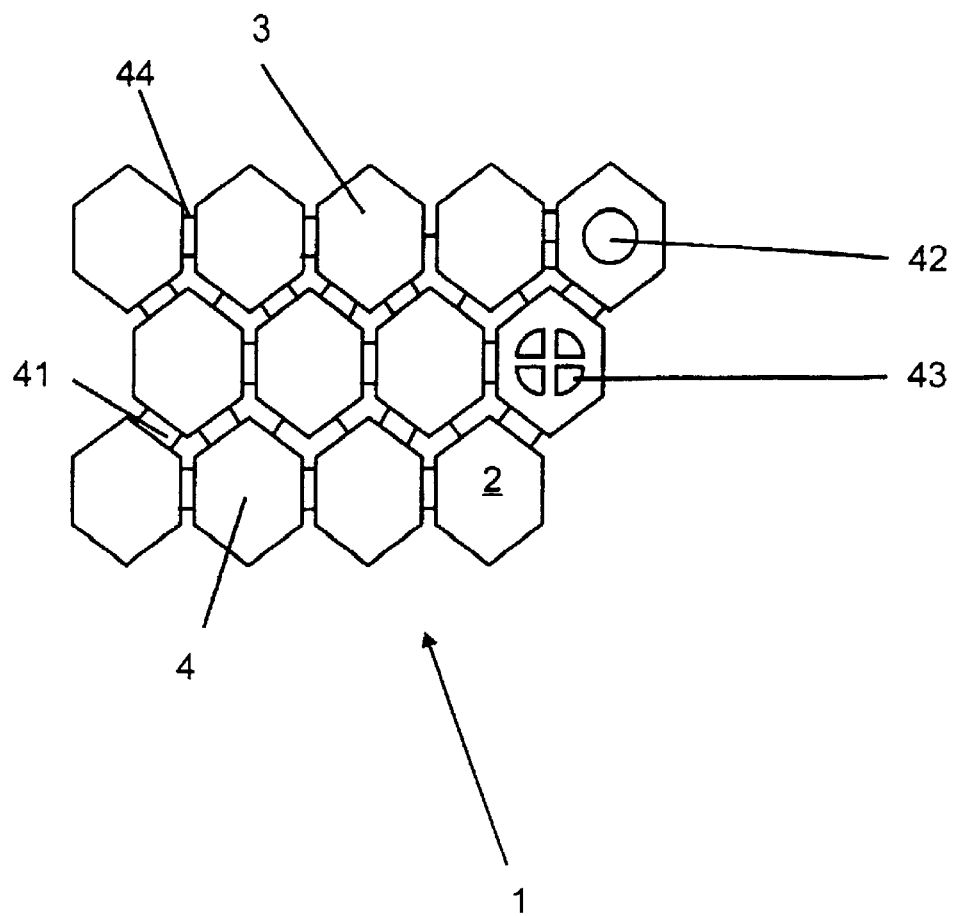
FIG. 1 shows a section of the bandage of the invention.

FIG. 1 shows a section of the bandage 1 of the invention. The bandage 1 consists of a flexible carrier 2 to one side of which is applied a self-adhesive coating 3, which is in fact a hotmelt self-adhesive composition.

The carrier has a large number of apertures 41, giving rise to individual segments 4 which, in turn, are linked to one another by way of connecting bridges 44.

The segments 4 are arranged in a pattern and are in the form of regular hexagons.

To save on weight, the segments 4 can also be provided in various forms with cutouts 42, 43; for instance, the cutouts 42, 43 can be circular or, preferably, segmented in form.

Figure 2:
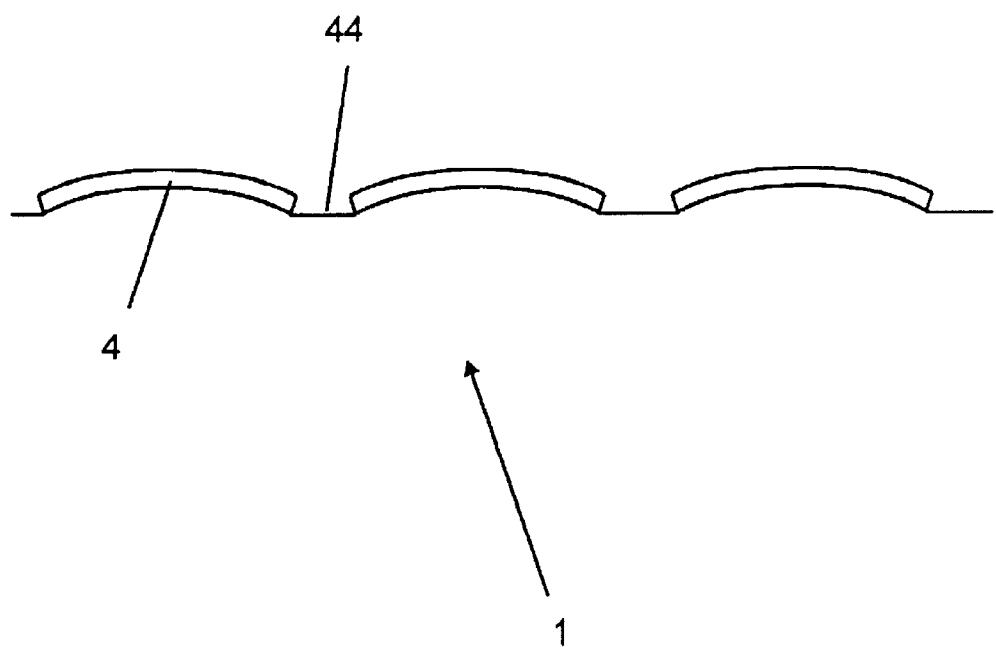
FIG. 2 shows the bandage in lateral section.

FIG. 2 shows the bandage 1 in lateral section.

The segments 4 have a convex form, so that when a dressing 5 is later wound with the bandage 1 the contact between the individual segments 4 is improved.

Figure 3:
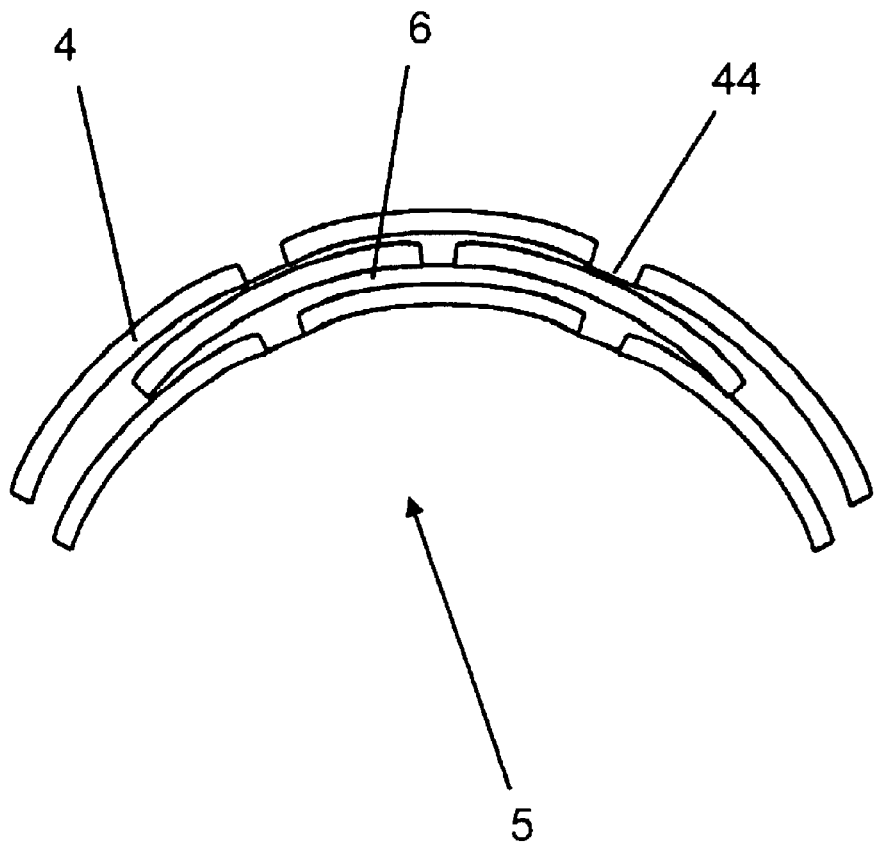
FIG. 3 shows a section of a multi-ply dressing formed with the bandage of the invention.

A dressing 5 of this kind is shown in section in FIG. 3. Because of the multi-ply winding of the dressing 5 there is overlapping of the segments 4, thus giving rise to a very stable dressing 5 around the body part to be treated. The stability is increased in this case by briefly heating the dressing 5 following its application, using, for example, a hot-air hairdryer. The hotmelt adhesive composition partially melts, and its bond strength is considerably increased as a result. On cooling, the individual segments 4 are connected with the respective overlying ply of the bandage 1 to form a solid dressing 5.

Bridges 6 of adhesive, which strengthen the dressing 5, form between the individual segments 4 and the underlying ply of the bandage.

The dressing 5 is removed by heating it again, which leads to a reduction in the bond strength.

Figure 4:
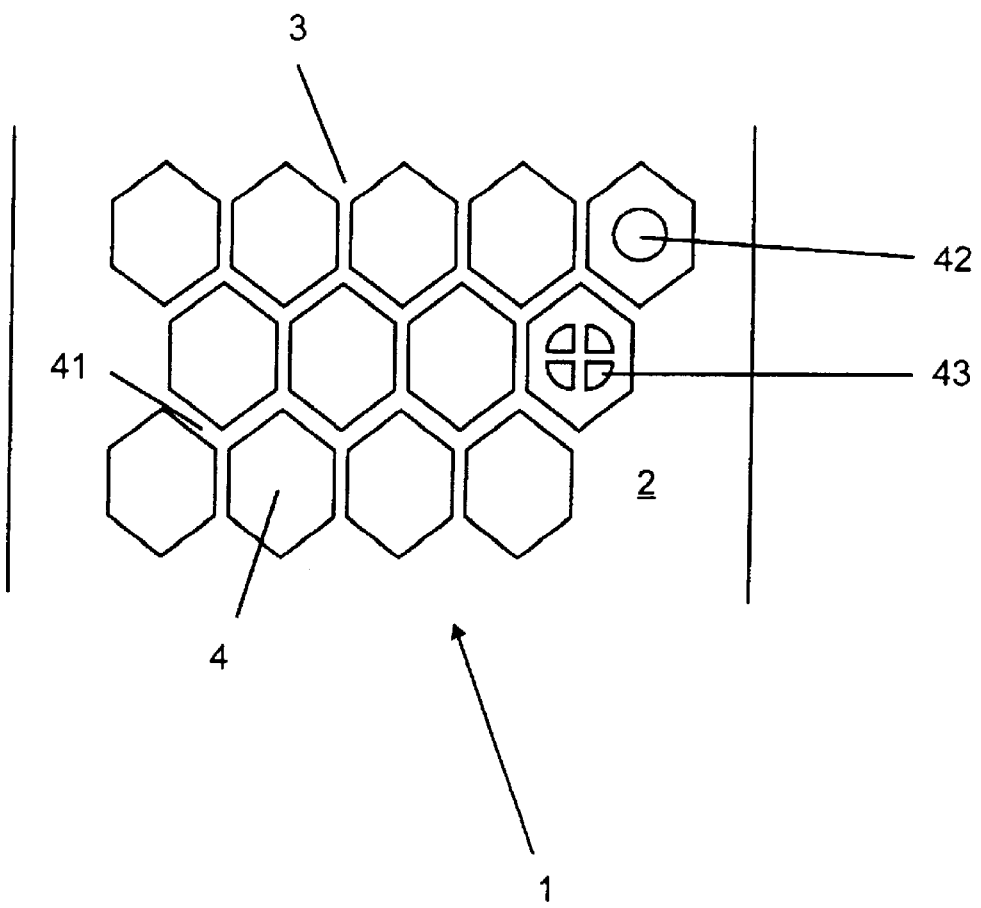
FIG. 4 shows the bandage with an auxiliary carrier and without connecting bridges.

FIG. 4, finally, shows a further section of the bandage 1 of the invention. The bandage 1 consists of a flexible carrier 2 to both sides of which a self-adhesive coating 3 is applied, specifically a hotmelt self-adhesive composition.

The carrier has a large number of apertures 41, thus giving rise to individual segments 4 which in this case, however, are not linked to one another by way of connecting bridges 44.

Instead, the stability of the bandage 1 is ensured by an auxiliary carrier 21. The individual segments 4 adhere to the auxiliary carrier 21.

The segments 4 are arranged in the pattern known from FIG. 1.

To save on weight, the segments 4, can, also here, be provided in various forms with cutouts 42, 43; for instance, the cutouts 42, 43 can be circular or, preferably, segmented in form.

What is claimed is:

1. A self-adhesive bandage comprising:
   a) a plurality of spaced apart, discontinuous, flexible carrier segments, wherein each carrier segment is a regular polygon;

b) a plurality of connecting bridges connecting said spaced apart, discontinuous, flexible carrier segments to one another; and c) a self-adhesive coating on at least one side of said spaced apart, discontinuous, flexible carrier segments.

2. A self-adhesive bandage comprising a flexible carrier and further comprising:

a) an auxiliary carrier;

b) a plurality of spaced apart, discontinuous, flexible carrier segments attached to said auxiliary carrier, wherein each carrier segment is a regular polygon; and c) self-adhesive coatings on both sides of said spaced apart, discontinuous, flexible carrier segments.

3. The self-adhesive bandage according to claim 2, wherein the carrier comprises an olefin film.

4. The self-adhesive bandage according to claim 2, wherein the carrier comprises a polyurethane foam.

5. The self-adhesive bandage according to claim 2, wherein the segments are convex in form.

6. The self-adhesive bandage according to claim 2, wherein the segments are in the form of hexagons.

7. The self-adhesive bandage according to claim 2, wherein the segments contain recesses.

8. The self-adhesive bandage according to claim 2, wherein the segments contain apertures.

9. The self-adhesive bandage according to claim 2, wherein the self-adhesive coating is applied to both sides of the flexible carrier.

10. The self-adhesive bandage according to claim 9, wherein the self-adhesive coating is a hotmelt adhesive composition having an activation temperature of less than 70° C.

11. The self-adhesive bandage according to claim 10, wherein the self-adhesive coating is a hotmelt adhesive composition having an activation temperature from 50 to 60° C.

12. The self-adhesive bandage according to claim 2, wherein the width of the bandage is between 4 and 15 cm.

13. The self-adhesive bandage according to claim 2, wherein the carrier is covered on its self-adhesive side with an anti-adhesive material.

14. The self-adhesive bandage according to claim 13, wherein the anti-adhesive material is a sheet of material that has been given an anti-adhesive finish.

15. The self-adhesive bandage according to claim 2, wherein the carrier is covered on one side with an auxiliary carrier.

16. The self-adhesive bandage according to claim 15, wherein the auxiliary carrier comprises a material which is non-elastic in the lengthwise direction, and optionally elastic in the traverse direction.

17. The self-adhesive bandage according to claim 15, wherein the auxiliary carrier is a woven or knit material.

18. The self-adhesive bandage according to claim 15, wherein the auxiliary carrier comprises cotton.

19. A method for stabilizing a joint or extremity, that comprises winding the bandage according to claim 2 around the joint or extremity to be stabilized.

20. The method according to claim 19, further comprising the step of heating the self-adhesive coating of the bandage to melt the self-adhesive coating, and then allowing the self-adhesive coating to cool to form a rigid dressing.

21. The method according to claim 19, further comprising the step of placing a splinting material selected from the group consisting of rails, compressible cushions, wovens, and nonwovens on the skin below the bandage before winding the bandage around the joint or extremity.

* * * * *